(12) United States Patent
Park et al.

(10) Patent No.: US 11,077,429 B2
(45) Date of Patent: Aug. 3, 2021

(54) CATALYST COMPOSITE FOR CONVERSION OF METHANE GAS AND METHOD FOR CONVERTING METHANE GAS USING THE SAME

(71) Applicant: INDUSTRY-ACADEMIC COOPERATION FOUNDATION, YONSEI UNIVERSITY, Seoul (KR)

(72) Inventors: Jong Hyeok Park, Seoul (KR); Jiwon Kim, Gyeonggido (KR); Ming Ma, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 167 days.

(21) Appl. No.: 16/233,686

(22) Filed: Dec. 27, 2018

(65) Prior Publication Data

US 2019/0224650 A1 Jul. 25, 2019

(30) Foreign Application Priority Data

Dec. 29, 2017 (KR) .......................... 10-2017-0183449

(51) Int. Cl.
*B01J 23/75* (2006.01)
*B01J 35/00* (2006.01)
(Continued)

(52) U.S. Cl.
CPC ............. *B01J 23/75* (2013.01); *B01J 21/066* (2013.01); *B01J 21/18* (2013.01); *B01J 23/755* (2013.01);
(Continued)

(58) Field of Classification Search
CPC ........ B01J 21/066; B01J 21/18; B01J 23/005; B01J 23/75; B01J 23/755; B01J 35/0033; B01J 35/006; C25B 3/23
(Continued)

(56) References Cited

U.S. PATENT DOCUMENTS 3,736,267 A * 5/1973 Bart .......................... B01J 21/10
502/328
4,957,896 A * 9/1990 Matsumoto .............. B01J 23/63
502/304

(Continued)

FOREIGN PATENT DOCUMENTS

KR   1006068560000        8/2006
WO   WO 2017/182923   * 10/2017 ............... C25B 1/04

OTHER PUBLICATIONS

Ming Ma et al., "Electrochemical CH4 oxidation into acids and ketones on ZrO2:NiCo2O4 quasi-solid solution nanowire catalyst." Applied Catalysis B: Environmental 259, pp. 1-9. (Year: 2019).*

(Continued)

*Primary Examiner* — Patricia L. Hailey
(74) *Attorney, Agent, or Firm* — Duane Morris LLP; Gregory M. Lefkowitz; Brandon A. Chan

(57) ABSTRACT

The present disclosure relates to a catalyst composite for conversion of methane gas, which includes $Co_3O_4$ nanoplates and $ZrO_2$ nanoparticles adsorbed to the surface of the $Co_3O_4$ nanoplates, and is used for converting methane gas into alcohols, and a method for conversion of methane gas using the same. When using the catalyst composite, it is possible to convert methane gas into alcohols with high efficiency under a mild condition of room temperature and ambient pressure.

17 Claims, 14 Drawing Sheets

(51) Int. Cl.
*B01J 21/06* (2006.01)
*B01J 21/18* (2006.01)
*B01J 23/755* (2006.01)
*B01J 37/00* (2006.01)
*B01J 37/34* (2006.01)
*B01J 37/03* (2006.01)
*C25B 3/23* (2021.01)
*C07C 49/08* (2006.01)
*C07C 27/10* (2006.01)
*C07C 31/04* (2006.01)
*C07C 31/08* (2006.01)
*C07C 31/10* (2006.01)

(52) U.S. Cl.
CPC ......... *B01J 35/006* (2013.01); *B01J 35/0013* (2013.01); *B01J 35/0033* (2013.01); *B01J 37/009* (2013.01); *B01J 37/033* (2013.01); *B01J 37/343* (2013.01); *C25B 3/23* (2021.01); *B01J 2523/48* (2013.01); *C07C 27/10* (2013.01); *C07C 31/04* (2013.01); *C07C 31/08* (2013.01); *C07C 31/10* (2013.01); *C07C 49/08* (2013.01)

(58) Field of Classification Search
USPC ........ 502/182, 185, 337, 349, 524; 428/546, 428/615; 205/452; 504/157.9
See application file for complete search history.

(56) References Cited

U.S. PATENT DOCUMENTS

| 5,314,673 | A | * | 5/1994 | Anseth | B01D 53/8628 |
| | | | | | 423/239.1 |
| 6,071,476 | A | * | 6/2000 | Young | G01N 25/30 |
| | | | | | 422/51 |
| 6,361,896 | B1 | * | 3/2002 | Eberle | C01B 3/583 |
| | | | | | 429/412 |
| 9,480,974 | B2 | | 11/2016 | Rajaram et al. | |
| 2008/0248373 | A1 | * | 10/2008 | Son | H01M 4/926 |
| | | | | | 429/482 |
| 2012/0095268 | A1 | * | 4/2012 | Tonkovich | C01B 3/384 |
| | | | | | 568/449 |
| 2013/0071761 | A1 | * | 3/2013 | Amine | H01M 4/8605 |
| | | | | | 429/405 |

OTHER PUBLICATIONS

Cheoulwoo Oh et al., "Electrocatalytic methane oxidation on Co3O4-incorporated ZrO2 nanotube powder." Applied Catalysis B: Environmental 283, pp. 1-8. (Year: 2021).*
Derek Pletcher et al., "Comparison of the Spinels Co3O4 and NiCo2O4 as Bifunctional Oxygen Catalysts in Alkaline Media." Electrochimica Acta 188, pp. 286-293. (Year: 2016).*
F. Wyrwalski et al., "Modified Co3O4/ZrO2 catalysts for VOC emissions abatement." Catalysis Today 119, pp. 332-337. (Year: 2007).*
Xianglan Xu et al., "Promotional effects of samarium on Co3O4 spinel for CO and CH4 oxidation." Journal of Rare Earths, vol. 32, No. 2, pp. 159-169. (Year: 2014).*
P. Rybak et al., "Conversion of ethanol over supported cobalt oxide catalysts." Catalysis Today 176, pp. 14-20. (Year: 2011).*
Ma et al., "Ultrahigh Electrocatalytic Conversion of Methane at Room Temperature", Adv. Sci. Sep. 2017, 8 pages.
Ma et al., "Structure and Surface Modifications of Photoanodes Materials for Solar Energy Utilization", Jun. 2017, 117 pages.
Du et al., "The role of zirconia in cobaltosic oxide catalysts for low-temperature CO oxidation", RSC Adv., (2016) 6, 111070.
Ercolino et al., "Pd/Co3O4-based catalysts prepared by solution combustion synthesis for residual methane oxidation in lean conditions", Catalysis Today, 257 (2015), 66-71.
Pu et al., "Catalytic combustion of lean methane at low temperature over ZrO2-modified Co3O4 catalysts", Applied Surface Science, 422, Jun. 3, 2017, pp. 85-93.
Sun et al., "Exploring the Effect of Co3O4 Nanocatalysts with Different Dimensional Architectures on Methane Combustion", ChemCatChem, 8, 2016, pp. 540-545.
Puangjan et al., "An efficient ZrO2/Co3O4/reduced graphene oxide nanocomposite electrochemical sensor for simultaneous determination of gallic acid, caffeic acid and protocatechuic acid natural antioxidants", Electrochimica Acta, 211, May 19, 2016, pp. 273-288.

* cited by examiner

CATALYST COMPOSITE FOR CONVERSION OF METHANE GAS AND METHOD FOR CONVERTING METHANE GAS USING THE SAME

CROSS-REFERENCE TO RELATED APPLICATIONS

This application claims, under 35 U.S.C. § 119, the priority of Korean Patent Application No. 10-2017-0183449 filed on Dec. 29, 2017 in the Korean Intellectual Property Office, the disclosure of which is incorporated herein by reference in its entirety.

TECHNICAL FIELD

The following disclosure relates to a catalyst composite for conversion of methane gas and a method for converting methane gas using the same. More particularly, the following disclosure relates to a catalyst composite for conversion of methane gas by which activation energy of methane is reduced and the potential of an electrode is controlled to produce alcohols with high efficiency even at room temperature under ambient pressure, as well as to a method for converting methane gas using the same.

BACKGROUND

Methane is an important ingredient which occupies 21.4% of main energy sources of natural gas and is important fuel used for industrial or living applications. As compared to the other fossil fuels, such as petroleum or coal, methane emits carbon dioxide in a relatively small amount upon the combustion of natural gas. Therefore, methane is very suitable for substitute energy until a carbon-free energy source is developed sufficiently. However, emission of methane gas has been ignored even though it has an effect upon a greenhouse effect potentially to at least 30 times of the effect of carbon dioxide, and has been regarded as an insignificant problem. Particularly, global warming and development of shale gas aggravate emission of methane gas. Recently, due to environmental pollution and a climate change, negative effects of methane emission have been spotlighted. Therefore, many efforts have been made to convert methane in the air to the level of carbon dioxide through a thermal catalyst or photocatalyst. However, the conventional process for conversion of methane still has problems, including the use of an expensive metal catalyst, high reaction temperature, excessively low conversion efficiency, or the like.

In this context, oxidation and conversion of methane into liquid alcohols, such as methanol, ethanol or propanol, is more economic and energy-efficient. Among the liquid alcohols, alcohols having high energy density have been applied widely and developed into commercial products.

As a methane conversion product, methanol has been studied actively. Currently, reaction of syngas is an important route for industrial production of methanol and such syngas is produced through modification of methane vapor. The following two reaction schemes illustrate a process of converting methane into methanol.

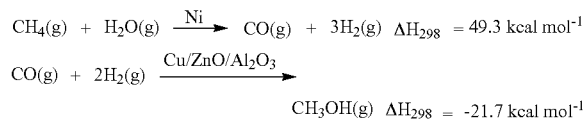

According to the reaction schemes, the energy required for modifying syngas in the first reaction is higher than the energy emission from the second reaction, which suggests that additional energy is required for converting methane into methanol. Some scientists carried out conversion of methane into methanol under the ambient condition through bacteria known as methanotrophs. The method requires a complicated process, additional energy consumption or culture of enzymes and suitable control of culturing conditions, and thus has a problem of degradation of conversion efficiency.

Therefore, there is a need for a technology of converting methane into alcohols with high efficiency at room temperature under ambient pressure without using the conventional inefficient uneconomical methane conversion technology.

REFERENCES

Patent Documents (Patent Document 1) Korean Patent Publication No. 10-0606856
(Patent Document 2) U.S. Pat. No. 9,480,974

SUMMARY

The present disclosure is designed to solve the problems of the related art, and an embodiment of the present disclosure is directed to converting methane gas efficiently into alcohols by carrying out electrochemical oxidation of methane gas at room temperature under ambient pressure. Thus, the present disclosure is directed to providing a method for converting methane gas into 2-propanol and 1-propanol with a high conversion efficiency of 60% or more by carrying out nucleophilic addition and free radical addition using a carbonate electrolyte and $ZrO_2/Co_3O_4$ nanocomposite as a catalyst.

In one aspect, there is provided a catalyst composite for conversion of methane gas, which includes: $Co_3O_4$ nanoplates or $NiCo_2O_4$ nanowires; and $ZrO_2$ nanoparticles adsorbed to the surface of the $Co_3O_4$ nanoplates or $NiCo_2O_4$ nanowires, and is used for converting methane gas into alcohols.

When the support is $Co_3O_4$ nanoplates, the elemental ratio of Co to Zr in the catalyst composite may be 0.2:1-6.5:1.

Preferably, the elemental ratio of Co to Zr in the catalyst composite may be 0.4:1-0.5:1.

When the support is $NiCo_2O_4$ nanowires, the elemental ratio of Zr:Ni:Co in the composite may be 0.1-2.5:2-3:5.

The molar compositional ratio of the $Co_3O_4$ nanoplates or $NiCo_2O_4$ nanowires to the $ZrO_2$ nanoparticles is 1:0.1-1:10.

The $ZrO_2$ nanoparticles may have a spherical shape, rod-like shape, hollow shape, ellipsoidal solid shape, or the like.

The $ZrO_2$ nanoparticles may have an average particle diameter of 10 nm-1 μm, and the $Co_3O_4$ nanoplates may have an average particle diameter of 1 μm-10 μm.

The catalyst composite may be formed by complexation through physical binding.

In another aspect, there is provided an electrochemical catalyst for conversion of methane gas, which includes: a conductive substrate selected from graphite paper, graphene, carbon black, copper, nickel and alumina; a catalyst composite layer for conversion of methane gas defined above, formed on the conductive substrate; and optionally, a cover layer for protecting the catalyst composite layer for conversion of methane gas.

In still another aspect, there is provided a method for preparing a catalyst composite for conversion of methane gas, including the steps of: (a) introducing $ZrOCl_2$ hydrate, $Co(NO_3)_2$ hydrate and hydroxide to water and dissolving them therein to obtain an aqueous precursor solution; (b) heating the aqueous precursor solution to 150-250° C. to precipitate $ZrO_2/Co_3O_4$ composite powder; (c) carrying out centrifugal separation of the product of step (b) to obtain $ZrO_2/Co_3O_4$ powder; and (d) washing the $ZrO_2/Co_3O_4$ powder of step (c) and carrying out heat treatment at 400-600° C. to obtain a $ZrO_2/Co_3O_4$ catalyst composite.

The hydroxide may be any one selected from Na(OH), K(OH), $Ca(OH)_2$ and $Sr(OH)_2$.

The $ZrOCl_2$ hydrate and $Co(NO_3)_2$ hydrate may be mixed at a molar compositional ratio of 1:1-1:6.

In yet another aspect, there is provided a method for conversion of methane gas, including: carrying out electrochemical oxidation of methane gas in the presence of a conductive graphite electrode surface-coated with the $ZrO_2/Co_3O_4$ catalyst composite and a carbonate electrolyte to convert methane gas into alcohols.

The coating may be carried out by adding a dispersion of the $ZrO_2/Co_3O_4$ catalyst composite in water to a graphite electrode, followed by drying.

The electrode surface-coated with the $ZrO_2/Co_3O_4$ catalyst composite may be further coated with a protective layer on the catalyst composite layer.

A step of removing oxygen may be further carried out through bubbling of methane in a carbonate electrolyte before the electrochemical oxidation.

The final product obtained by the electrochemical oxidation may include at least one selected from 1-propanol, 2-propanol, methanol, formaldehyde, ethanol, acetaldehyde and acetone.

Among the final products, 1-propanol and 2-propanol may be produced from acetaldehyde.

1-propanol and 2-propanol may be produced through nucleophilic addition and free radical addition.

The electrochemical oxidation may be carried out at room temperature under ambient pressure.

The electrochemical oxidation may be carried out under pressure to increase the solubility of methane.

According to the method for converting methane gas of the present disclosure, it is possible to convert methane gas into 2-propanol and 1-propanol with a high conversion efficiency of 60% or more by carrying out nucleophilic addition and free radical addition using a carbonate electrolyte and $ZrO_2/Co_3O_4$ nanocomposite as a catalyst in order to convert methane gas efficiently into alcohols through electrochemical oxidation of methane gas at room temperature under ambient pressure. Therefore, the present disclosure provides a method for converting methane occupying 70% or more of shale gas into useful alcohols with ease in a cost-efficient manner, and thus is very useful for the petrochemical industry hereafter.

DETAILED DESCRIPTION OF EMBODIMENTS

Figure 1:
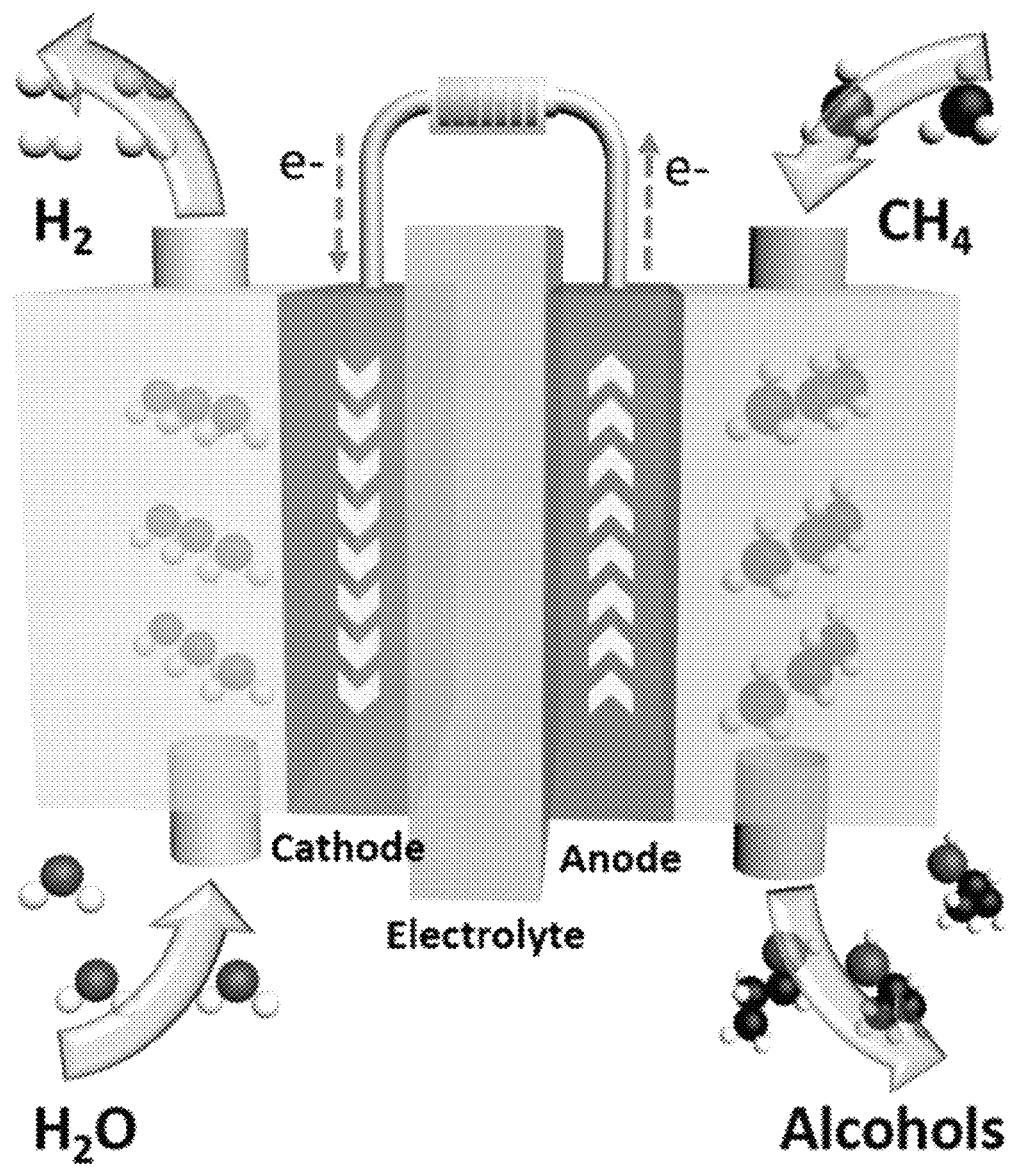
FIG. 1 is a schematic view illustrating a process of methane conversion through electrochemical oxidation.

Hereinafter, various aspects and embodiments of the present disclosure will be explained in more detail.

Exemplary embodiments now will be described more fully hereinafter with reference to the accompanying drawings.

The present disclosure may, however, be embodied in many different forms and should not be construed as limited to the exemplary embodiments set forth therein. In the description, details of well-known features and techniques may be omitted to avoid unnecessarily obscuring the presented embodiments.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. Furthermore, the use of the terms a, an, etc. does not denote a limitation of quantity, but rather denotes the presence of at least one of the referenced item. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Hereinafter, the catalyst composite for conversion of methane gas according to the present disclosure will be described.

The catalyst composite for conversion of methane gas includes: $Co_3O_4$ nanoplates or $NiCo_2O_4$ nanowires; and $ZrO_2$ nanoparticles adsorbed to the surface of the $Co_3O_4$ nanoplates or $NiCo_2O_4$ nanowires, and is used for converting methane gas into alcohols.

Preferably, the molar compositional ratio of the $Co_3O_4$ nanoplates or $NiCo_2O_4$ nanowires to the $ZrO_2$ nanoparticles is 1:0.1-1:10, more preferably 1:2-1:8, and even more preferably 1:3-1:6.

The elemental ratio of Co to Zr in the catalyst composite is preferably 0.2:1-6.5:1. When the ratio is not within the above-defined range, the properties of the catalyst are changed significantly and conversion of methane gas ratio is reduced rapidly. Thus, it is important to provide the above-defined elemental ratio.

More preferably, the elemental ratio of Co to Zr in the catalyst composite is preferably 0.4:1-0.5:1. Particularly, when the elemental ratio of Co to Zr is 0.4:1-0.5:1, it is possible to maximize current density, and thus to improve electrochemical methane conversion efficiency significantly.

The $ZrO_2$ nanoparticles may have a spherical shape, rod-like shape, hollow shape, ellipsoidal solid shape, or the like. Preferably, the $ZrO_2$ nanoparticles have an average particle diameter of 10 nm-1 μm.

In addition, the $Co_3O_4$ nanoplates preferably have an average particle diameter of 1 μm-10 μm. Since bulk $Co_3O_4$ has a particle diameter of about 10 μm and the particle size of $Co_3O_4$ particles is decreased as the ratio of $ZrO_2$ is increased, the average particle diameter becomes 1 μm-10 μm.

The catalyst composite may be formed by complexation through physical binding. Since the composite is formed merely by physical adsorption not by chemical binding, it is possible to obtain an advantageous effect in terms of electrochemical methane conversion efficiency.

Hereinafter, the electrochemical catalyst for conversion of methane gas according to the present disclosure will be explained.

The electrochemical catalyst for conversion of methane gas according to the present disclosure includes: a conductive substrate selected from graphite paper, graphene, carbon black, copper, nickel and alumina; a catalyst composite layer for conversion of methane gas formed on the conductive substrate; and optionally, a cover layer for protecting the catalyst composite layer for conversion of methane gas.

Hereinafter, a method for preparing the composite catalyst for conversion of methane gas according to the present disclosure, particularly a composite catalyst for conversion of methane gas including $Co_3O_4$ nanoplates as a catalyst support, will be explained.

First, a Zr precursor (e.g. $ZrOCl_2$ hydrate), Co precursor (e.g. $Co(NO_3)_2$ hydrate) and hydroxide are introduced to water and dissolved therein to obtain an aqueous precursor solution (step a).

Preferably, the hydroxide may be any one selected from Na(OH), K(OH), $Ca(OH)_2$ and $Sr(OH)_2$, more preferably Na(OH), but the scope of the present disclosure is not limited thereto. Any hydroxide may be used as long as it can induce precipitation.

In addition, the $ZrOCl_2$ hydrate and $Co(NO_3)_2$ hydrate are mixed preferably at a molar compositional ratio of 1:1-1:6.

Next, the aqueous precursor solution is heated to 150-250° C. to precipitate a $ZrO_2/Co_3O_4$ composite powder (step b).

The heating may be carried out preferably at 160-220° C., more preferably 170-200° C. to precipitate the product.

After that, the product of step (b) is subjected to centrifugal separation to obtain $ZrO_2/Co_3O_4$ composite powder.

Then, the $ZrO_2/Co_3O_4$ composite powder of step (c) is washed and dried, and then heat treated at 400-600° C. to obtain a $ZrO_2/Co_3O_4$ catalyst composite.

More preferably, the heat treatment may be carried out at 450-550° C.

Hereinafter, a method for preparing the composite catalyst for conversion of methane gas according to the present disclosure, particularly a composite catalyst for conversion of methane gas including $NiCo_2O_4$ nanowires as a catalyst support, will be explained.

First, a Ni precursor (e.g. $NiCl_2$), Co precursor (e.g. $CoCl_2.H_2O$), Zr precursor ($ZrCl_4$), structure-forming agent (e.g. urea) and a surfactant (e.g. hexadecyltrimethylammonium bromide) are introduced to water and dissolved therein to obtain an aqueous precursor solution.

Next, the aqueous precursor solution is heated to 150-250° C. to precipitate a $ZrO_2/Co_3O_4$ composite powder. The heating is carried out preferably to 100-140° C. to precipitate the product. After that, the product obtained from the preceding step is subjected to centrifugal separation to obtain composite powder. Then, the resultant composite powder is washed and dried, and heat treated preferably at 400-600° C. to obtain a catalyst composite.

The $ZrO_2/Co_3O_4$ nanocomposite catalyst or $ZrO_2/NiCo_2O_4$ nanocomposite catalyst according to the present disclosure may be coated with graphene to improve catalytic activity, or the like, significantly.

A hydrothermal process may be used for graphene coating. For example, the $ZrO_2/Co_3O_4$ nanocomposite catalyst or $ZrO_2/NiCo_2O_4$ nanocomposite catalyst according to the present disclosure and graphene may be dissolved into water. Then, heat treatment may be carried out at high temperature under pressure, and then the product may be subjected to washing and drying.

FIG. 1 is a schematic view illustrating a process for ethane gas conversion using electrochemical oxidation. Hereinafter, the method for conversion of methane gas according to the present disclosure will be explained with reference to FIG. 1.

The method for conversion of methane gas according to the present disclosure includes converting methane gas into alcohols at a graphite electrode surface-coated with the $ZrO_2/Co_3O_4$ catalyst composite through electrochemical oxidation.

The coating may be carried out by adding a dispersion of the $ZrO_2/Co_3O_4$ catalyst composite in water to a graphite electrode, followed by drying.

The electrode surface-coated with the $ZrO_2/Co_3O_4$ catalyst composite may be further coated with a protective layer on the catalyst composite layer.

A step of dissolving methane into a carbonate electrolyte through bubbling of methane to remove oxygen may be further carried out, before the electrochemical oxidation.

The final product obtained by the electrochemical oxidation may include at least one selected from 1-propanol, 2-propanol, methanol, formaldehyde, ethanol, acetaldehyde and acetone, wherein the main product may include 1-propanol and 2-propanol.

Acetaldehyde is an important intermediate and may be used for producing 1-propanol and 2-propanol.

Herein, 1-propanol and 2-propanol may be produced through nucleophilic addition and free radical addition.

Although the electrochemical oxidation may be carried out at room temperature under ambient pressure, it may be carried out under pressure to increase the solubility of methane.

EXAMPLES

Example 1-1: Preparation of $ZrO_2/Co_3O_4$ Nanocomposite Catalyst

All of the ingredients were used without further treatment. The $ZrO_2/Co_3O_4$ nanocomposite was obtained through a precipitation process and hydrothermal process. To obtain the first sample ('1-2 $ZrO_2/Co_3O_4$ sample' or '1-2 sample'), 0.1611 g of $ZrOCl_2.8H_2O$ (99.0%, Junsei, Japan), 0.291 g of $Co(NO_3)_2.6H_2O$ (98%, Aldrich, US) and 9.6 g of NaOH (96%, Samchun, Korea) were dissolved in 40 mL of deionized water (DI) for 30 minutes under agitation. Then, the resultant solution was transferred to a 60 mL autoclave container and heated at 180° C. for 24 hours. Then, the solution was subjected to centrifugal separation to obtain powder and the powder was washed with deionized water three times. Finally, 1-2 $ZrO_2/Co_3O_4$ sample was obtained after carrying out thermal annealing at 500° C. for 4 hours.

The amount of $Co(NO_3)_2.6H_2O$ was varied without any change in the other conditions to obtain $ZrO_2/Co_3O_4$ nanocomposites having different compositions. Particularly, the amount of $Co(NO_3)_2.6H_2O$ was controlled to 0.582 g to obtain the second sample ('1-4 $ZrO_2/Co_3O_4$ sample' or '1-4 sample'), and to 0.873 g to obtain the third sample ('1-6 $ZrO_2/Co_3O_4$ sample' or '1-6 sample'). The elemental ratio of Co to Zr is about 0.28:1, about 0.45:1 and about 6.3:1 in 1-2 sample, 1-4 sample and 1-6 sample, respectively.

Example 1-2: Preparation of $ZrO_2/NiCo_2O_4$ Nanocomposite Catalyst

All of the ingredients were used without further treatment. The corresponding catalyst was obtained through a hydrothermal process. To obtain the first sample ('0.5-$ZrO_2$: $NiCo_2O_4$ sample' or '0.5 sample'), 0.322 g of $NiCl_2$ (98%, Sigma Aldrich), 1.19 g of $CoCl_2.H_2O$ (≥98%, Sigma Aldrich), 0.117 g of $ZrCl_4$ (≥99.5, Sigma Aldrich), 0.54 g of urea (99.0-100.5%, Alfa Aesar) and 0.728 g of hexadecyltrimethylammonium bromide (≥99%, Acros Organics) were dissolved in 40 mL of deionized water (DI) for 30 minutes under agitation, and then ultrasonication was carried out for 1 hour to mix them homogeneously. Then, the resultant solution was transferred to a 60 mL autoclave container and heated at 120° C. for 48 hours. Then, the solution was subjected to centrifugal separation to obtain powder and the powder was washed with deionized water six times. Finally, 0.5-$ZrO_2$:$NiCo_2O_4$ sample was obtained after carrying out thermal annealing at 500° C. for 3 hours.

The amount of $ZrCl_4$ was varied without any change in the other conditions to obtain catalysts having different compositions. Particularly, the amount of $ZrCl_4$ was controlled to 0.047 g to obtain the second sample ('0.2-$ZrO_2$:$NiCo_2O_4$ sample' or '0.2 sample'), to 0.234 g to obtain the third sample ('1.0-$ZrO_2$:$NiCo_2O_4$ sample' or '1.0 sample'), and to 0.468 g to obtain to 0.234 g to obtain the fourth sample ('2.0-$ZrO_2$:$NiCo_2O_4$ sample' or '2.0 sample'). The elemental ratio of Zr:Ni:Co is about 0.2:2.5:5, 0.5:2.5:5, 1:2.5:5, and 2:2.5:5 in 0.2 sample, 0.5 sample, 1.0 sample and 2.0 sample, respectively.

Example 1-3: Preparation of $ZrO_2/Co_3O_4$ Nanocomposite Catalyst Coated with Graphene The $ZrO_2/Co_3O_4$ nanocomposite according to Example 1-1 was coated with graphene to obtain a $ZrO_2/Co_3O_4$ nanocomposite catalyst coated with graphene.

To carry out coating with graphene, a hydrothermal process was used once again. Particularly, each of 1-2, 1-4 and 1-6 samples according to Example 1-1 and graphene were provided with a controlled weight ratio of 1:0.5, 1:1 and 1:2, and then dissolved in 40 mL of deionized water (DI) for 30 minutes under agitation in the same manner as described above. Then, the resultant solution was transferred to an autoclave container and heated at 180° C. for 24 hours. Then, the solution was subjected to centrifugal separation to obtain powder, and the powder was washed with deionized water three times. Finally, the resultant product was dried at 70° C.

Example 1-4: Preparation of $ZrO_2/NiCo_2O_4$ Nanocomposite Catalyst Coated with Graphene The $ZrO_2/NiCo_2O_4$ nanocomposite according to Example 1-2 was coated with graphene in the same manner as described in Example 1-3 to obtain a $ZrO_2/NiCo_2O_4$ nanocomposite catalyst coated with graphene.

Comparative Example 1: Preparation of $Co_3O_4$ Catalyst

A pure $Co_3O_4$ sample was obtained in the same manner as the preparation of 1-4 $ZrO_2/Co_3O_4$, except that no $ZrOCl_2.8H_2O$ was added to obtain a catalyst.

Comparative Example 2: Preparation of $ZrO_2/NiO$ Catalyst

A $ZrO_2/NiO$ sample was obtained in the same manner as the preparation of 1-4 $ZrO_2/Co_3O_4$, except that 0.582 g of $Ni(NO_3)_2.6H_2O$ (97%, Aldrich, US) was added instead of $Co(NO_3)_2.6H_2O$ to obtain a catalyst.

Example 2: Methane Conversion

Long-term electrochemical oxidation of methane was carried out in a two-electrode system including a closed reactor. Herein, graphite paper (Alfa) was used as a working electrode, Pt foil was used as a counter electrode and 30 mL of 0.5M $Na_2CO_3$ solution was used as an electrolyte (pH of about 12.0 before reaction, about 11.9 after reaction for 12 hours).

The working electrode was obtained by dispersing the catalyst composite powder sample according to Example 1 into deionized water at a concentration of 3 mg/mL under agitation for 30 minutes to form a dispersion, dropping 5.7 mL of the dispersion to graphite paper (20 $cm^2$) and carrying out drying at room temperature.

Next, 3 mL of 5% Nafion 117 solution was deposited onto graphite paper to cover the catalyst composite film and dried at room temperature. Before carrying out electrochemical reaction, oxygen was removed in the carbonate electrolyte for 1.5 hours and $CH_4$ gas was bubbled to dissolve $CH_4$ so that the space in the reactor might be filled with $CH_4$.

In this case, after the consumption of methane saturated in the aqueous solution, gaseous methane was dissolved in the electrolyte continuously to provide a sufficient amount of reactant. Electrochemical oxidation was carried out for 3, 6 or 12 hours at 2.0 V vs. Pt.

TEST EXAMPLES

Test Example 1: SEM and TEM Image Analysis of Catalyst

Figure 2A:
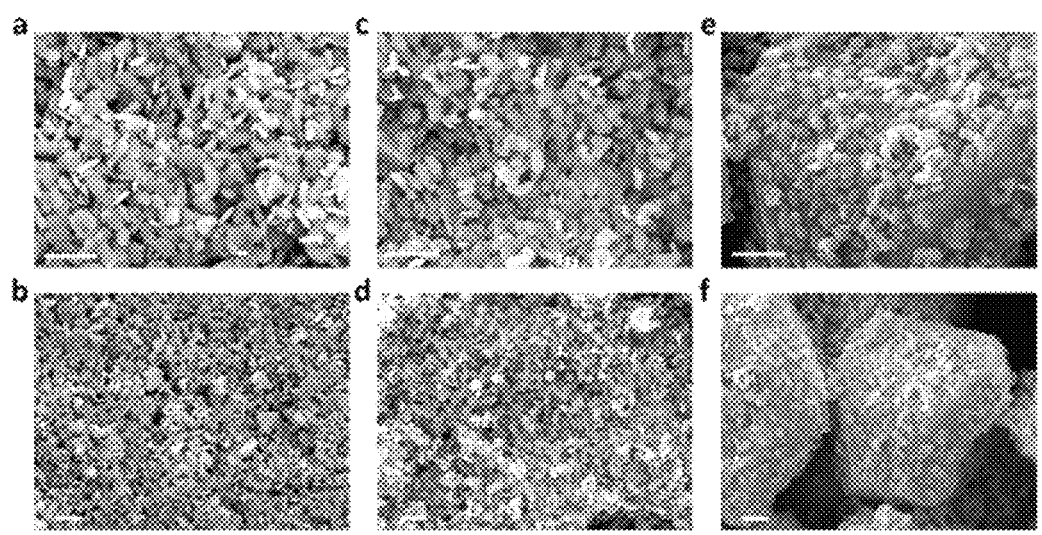
FIG. 2A is a scanning electron microscopic (SEM) image of the $ZrO_2/Co_3O_4$ catalyst nanocomposite according to the present disclosure.
Figure 2B:
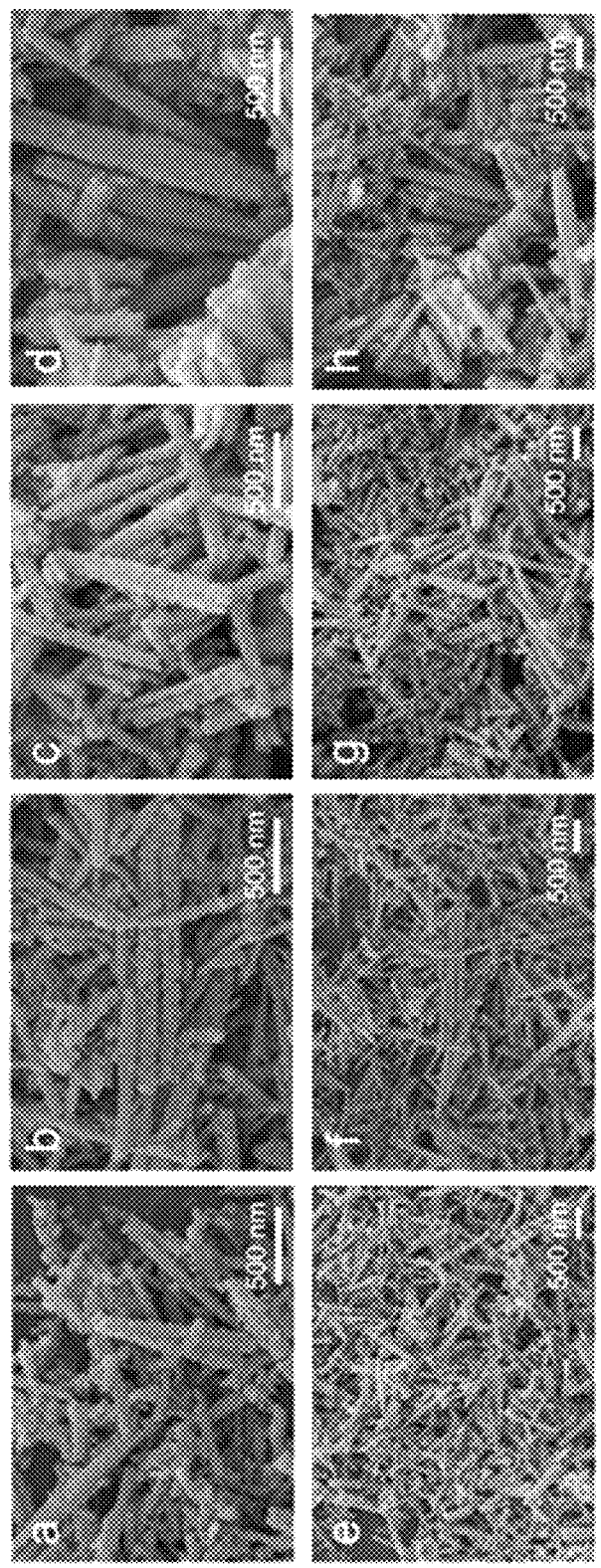
FIG. 2B is a SEM image of the $ZrO_2/NiCo_2O_4$ catalyst nanocomposite according to the present disclosure. Among the four types of nanocomposites obtained from Example 1-2, a) and e) are 0.2-$ZrO_2/NiCo_2O_4$ samples, b) and f) are 0.5-$ZrO_2/NiCo_2O_4$ samples, c) and g) are 1.0-$ZrO_2/NiCo_2O_4$ samples, and d) and h) are 2.0-$ZrO_2/NiCo_2O_4$ samples. It can be seen that the Ni—Co nano-alloy or nanocomposite support shows a nanowire shape and Zr oxide is adsorbed thereon. However, the diameter of nanowires tends to increase as the ratio of Zr increases.

The shapes of $ZrO_2/Co_3O_4$ nanocomposites (1-2 $ZrO_2/Co_3O_4$, 1-4 $ZrO_2/Co_3O_4$, and 1-6 $ZrO_2/Co_3O_4$) having different compositions were observed through scanning electron microscopy (SEM). The resultant images are shown in FIG. 2 (scale bar: 1 μm). It can be seen from FIG. 2 that oval nanoparticles of $ZrO_2$ having a uniform size are formed and adsorbed to the surface of $Co_3O_4$ plates in all of the samples. As the amount of $Co_3O_4$ is increased, the particle size of $Co_3O_4$ is increased gradually until it becomes bulk. This may affect the catalytic properties of $ZrO_2/Co_3O_4$ nanocomposites.

The pure $Co_3O_4$ particles according to Comparative Example 1 have a large particle diameter of 10 μm or more. The size of $Co_3O_4$ plates may be controlled by co-precipitation of $ZrO_2$.

As the amount of the Co precursor is increased, the Zr/Co ratio is decreased. In 1-6 $ZrO_2/Co_3O_4$ sample, the large $Co_3O_4$ plates are surrounded with small $ZrO_2$ particles, which causes a rapid drop in Zr/Co ratio.

Figure 3:
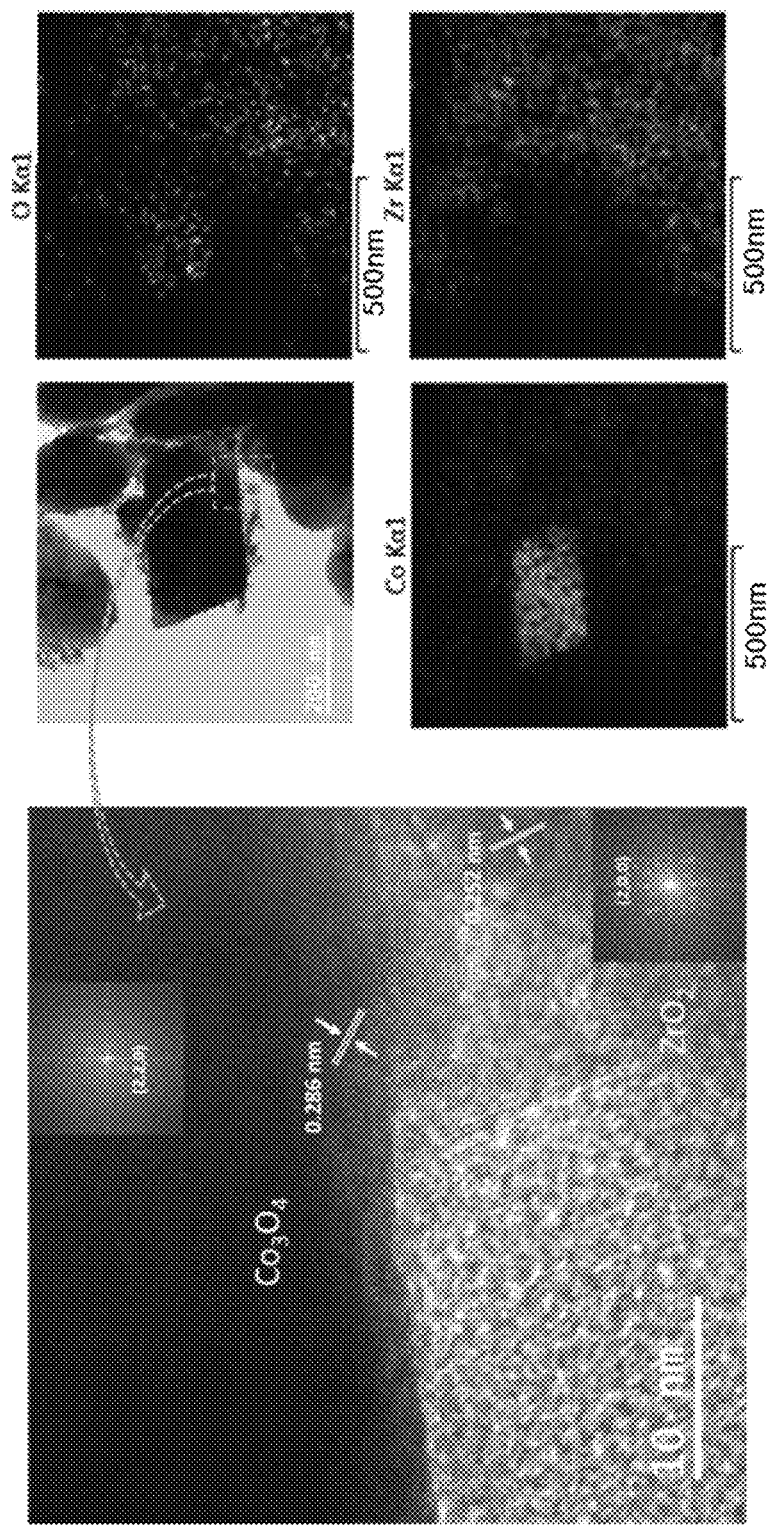
FIG. 3 is a transmission electron microscopic (TEM) image of the $ZrO_2/Co_3O_4$ nanocomposite according to the present disclosure.

FIG. 3 illustrates a transmission electron microscopic (TEM) image of 1-4 $ZrO_2/Co_3O_4$ nanocomposite. As shown in FIG. 3, $Co_3O_4$ plates are differentiated from $ZrO_2$ nanoparticles with ease. It is observed from the high-resolution (HR)-TEM image (a) that the lattice constant relates with (002) surface of $ZrO_2$ is 0.252 nm and the lattice constant related with (022) surface of $Co_3O_4$ is 0.286 nm. In addition, FIG. 3(b) shows the results of atomic mapping of Co, Zr and O. It can be seen from the elemental distribution that $Co_3O_4$ plates and $ZrO_2$ nanoparticles have a different structure. The SEM and TEM images show that $Co_3O_4$ and $ZrO_2$ form physical binding well. It is though that this may provide a synergic effect in electrochemical oxidation of $CH_4$.

Test Example 2: XRD and XPS Spectrum Analysis of Catalyst

Figure 4A:
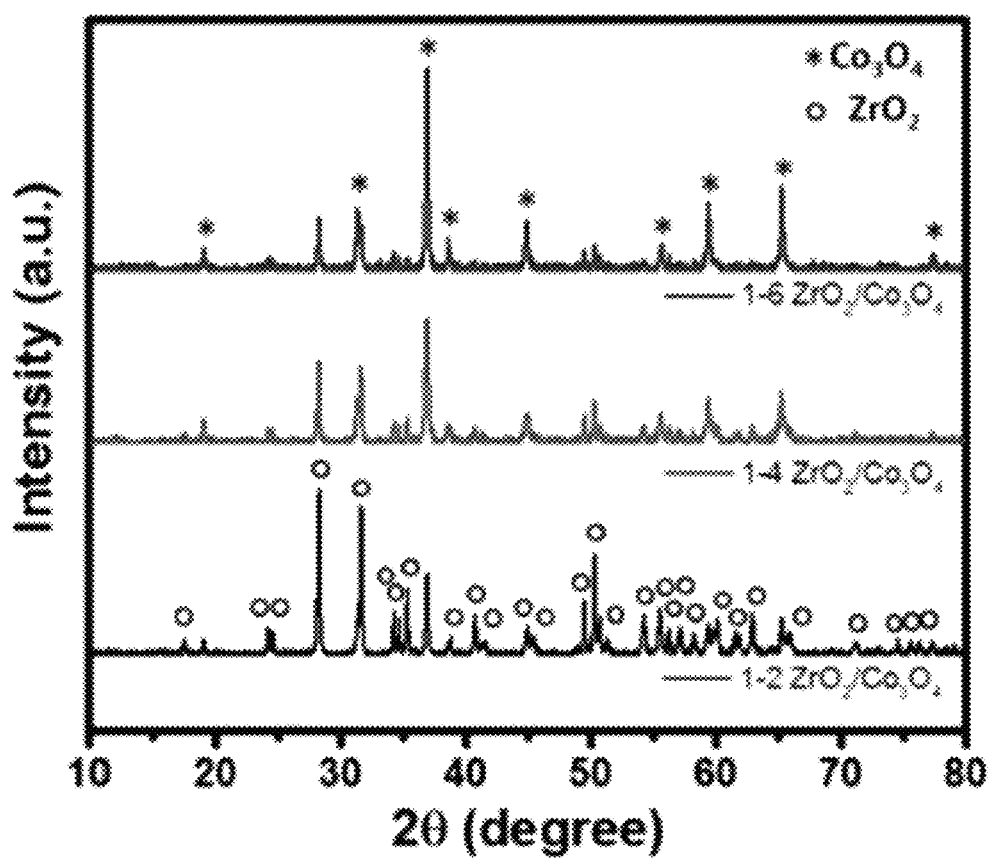
FIG. 4A shows the results of X-ray diffractometry (XRD) spectrum depending on the ratio of $ZrO_2$ to $Co_3O_4$ in the $ZrO_2/Co_3O_4$ nanocomposite according to Example 1.
Figure 4B:
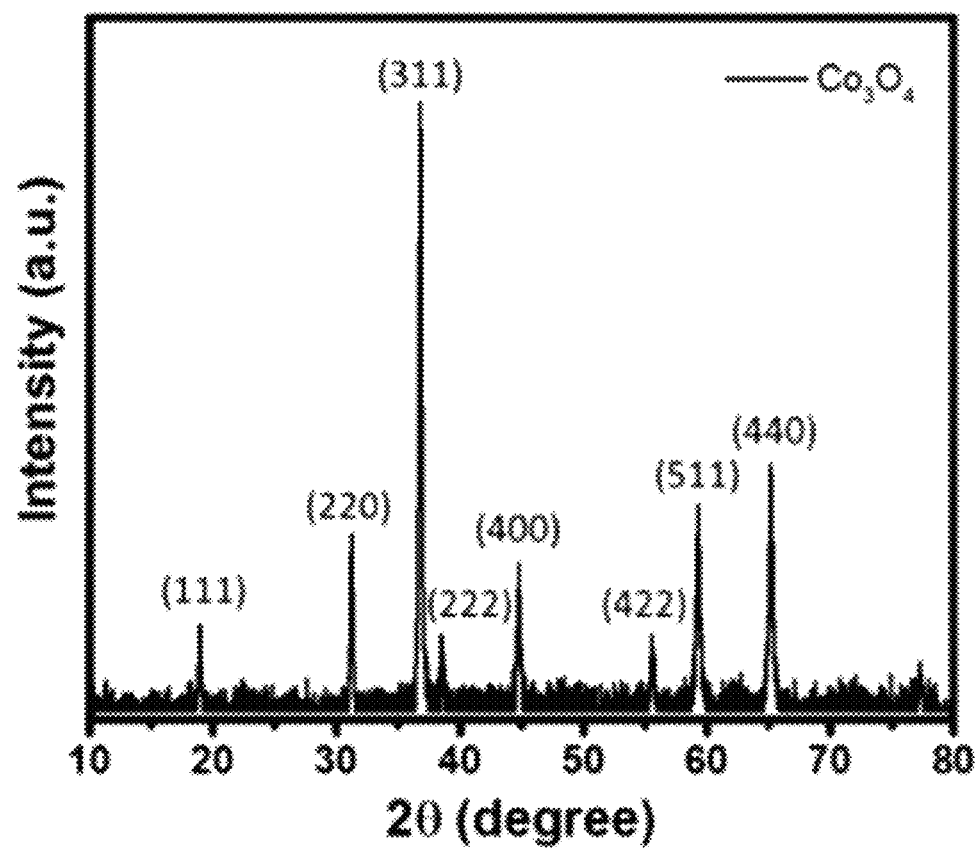
FIG. 4B shows the results of XRD spectrum of pure $Co_3O_4$ according to Comparative Example 1.
Figure 5A:
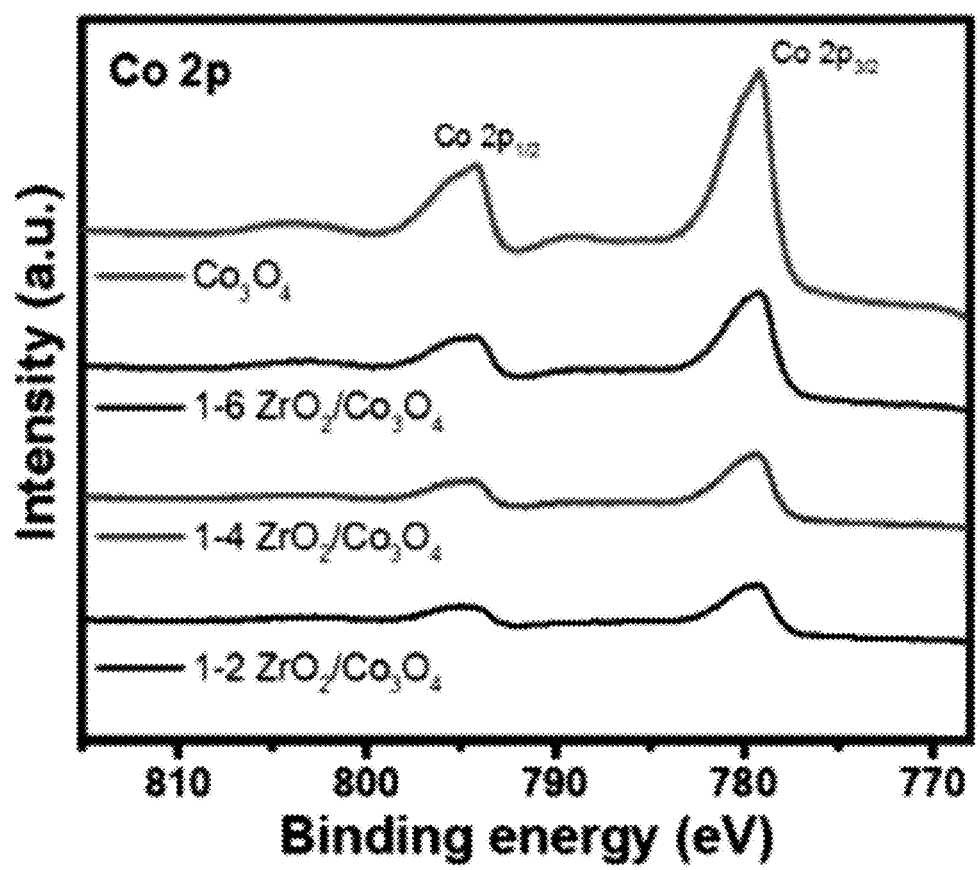
FIG. 5A-FIG. 5C show X-ray photoelectron spectroscopy (XPS) signals of the catalysts according to Example 1 and Comparative Example 1.
Figure 5B:
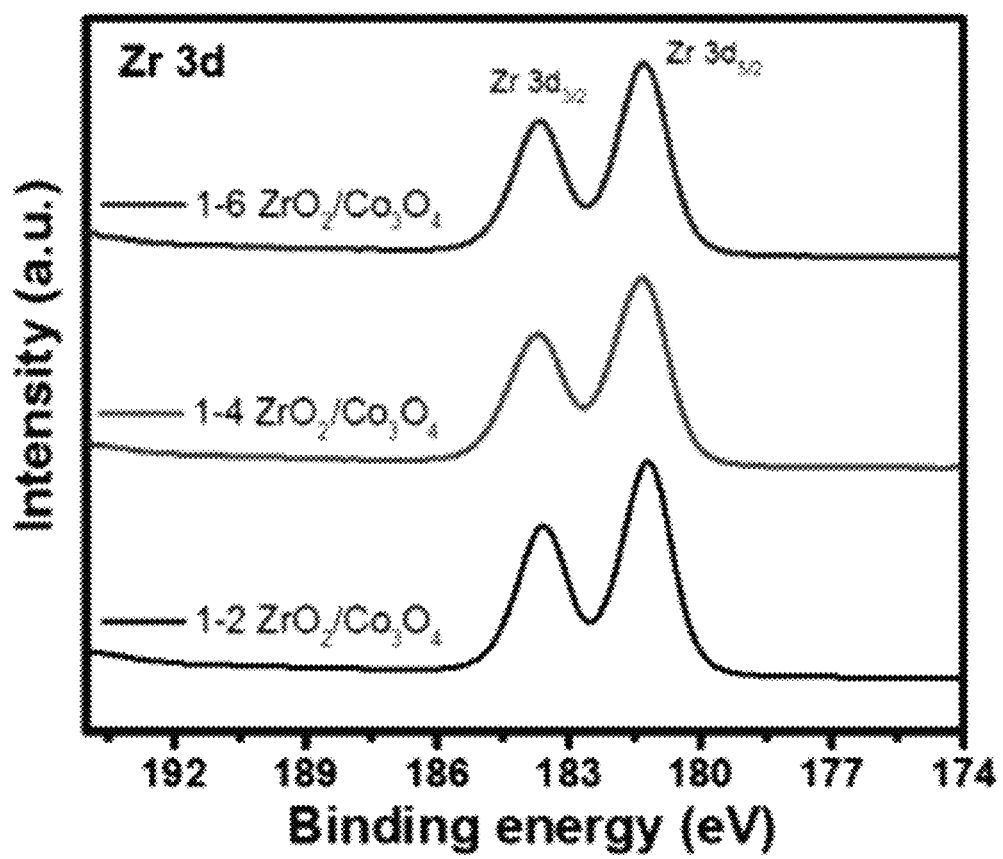
Figure 5C:
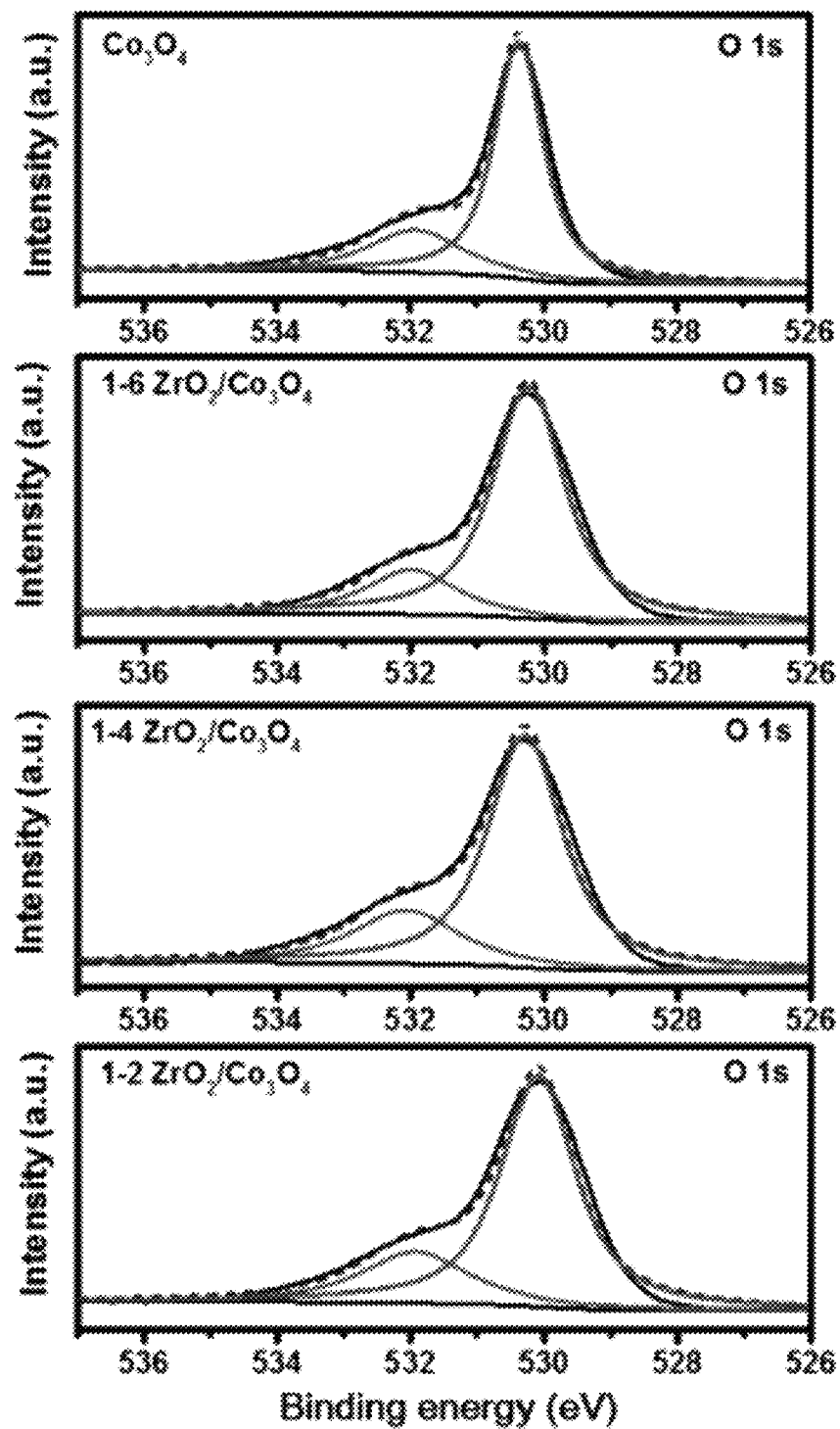

FIG. 4A shows the results of X-ray diffractometry (XRD) spectrum depending on the ratio of $ZrO_2$ to $Co_3O_4$ in the $ZrO_2/Co_3O_4$ nanocomposite according to Example 1, and FIG. 4B shows the results of XRD spectrum of pure $Co_3O_4$ according to Comparative Example 1. In addition, FIG. 5A-FIG. 5C show X-ray photoelectron spectroscopy (XPS) signals of the catalysts according to Example 1 and Comparative Example 1.

According to the results, the peaks of each sample appear substantially at the same position without a shift. No clear chemical binding is observed between $Co_3O_4$ and $ZrO_2$.

The crystal structures of $ZrO_2/Co_3O_4$ composites having different ratios were analyzed by XRD with Cu-Kα irradiation and compared with the crystal structure of pure $Co_3O_4$. The diffraction peaks of $ZrO_2$ are related with a monoclinic phase and those of $Co_3O_4$ are related with a cubic structure. In the XRD pattern, typical (001), (100), (011), (−111) and (022) surfaces of $ZrO_2$ are observed at 17.5°, 24.2°, 24.6°, 28.3° and 50.3°. The intensities of all related peaks became gradually decreased as the amount of $Co_3O_4$ increased. Typical (111), (311) and (440) surfaces of $Co_3O_4$ are observed at 19.0°, 36.9° and 65.2°, and show the same change in peak intensity according to the amount of $ZrO_2$. The above data explain the microstructure and crystal structure of each $ZrO_2/Co_3O_4$ nanocomposite. The surface state related with specific local selectivity of $CH_4$ oxidation can be explained through the XPS results of FIG. 5A-FIG. 5C. It is shown that the signal of Co—Zr binding energy does not undergo a significant shift according to a change in ratio of the constitutional ingredients. However, the intensities of Co signals are changed clearly according to a decrease in amount of Co. The Zr signals are also changed but are changed less significantly as compared to the Co signals. It is thought that this is because $ZrO_2$ is present on the $Co_3O_4$ surface. In addition, O 1s signal is affected. It is thought that O1s peaks at 530 eV and 532 eV are derived from the lattice oxygen and oxygen on the irregular surface, respectively. The peak at 532 eV is related with the chemical adsorption on the surface or a defect, such as dissociated oxygen or hydroxyl group. It is known that the $Co_3O_4$ surface is covered easily with a single layer of chemically adsorbed oxygen. In this case, a peak appears at 532 eV in O1s spectrum of pure $Co_3O_4$, which suggests the surface adsorption ability of $Co_3O_4$. In addition, after the co-precipitation of $ZrO_2$, O 1s signals of all of the $ZrO_2/Co_3O_4$ composites show enhanced peaks at 532 eV. Such results demonstrate the surface electron acceptability of $ZrO_2$ and suggest that strong adsorption of $Co_3^{2-}$ ions occur on the surface of $ZrO_2$ upon the electrochemical oxidation of methane.

Thus, the fact that $Co_3O_4$ nanoplates or $NiCo_2O_4$ nanowires form a composite with $ZrO_2$ nanoparticles merely by physical binding, not by chemical binding can be determined through XRD spectrum analysis. Since the complex is formed merely by physical adsorption, not by chemical binding, it is possible to obtain an advantageous effect in terms of electrochemical conversion efficiency of methane.

Test Example 3: Analysis of Electrochemical Performance of $CH_4$ Oxidation

To determine the electrochemical performance of $CH_4$ oxidation, a glassy carbon disc electrode was introduced to load a catalyst and used as a working electrode.

Figure 6:
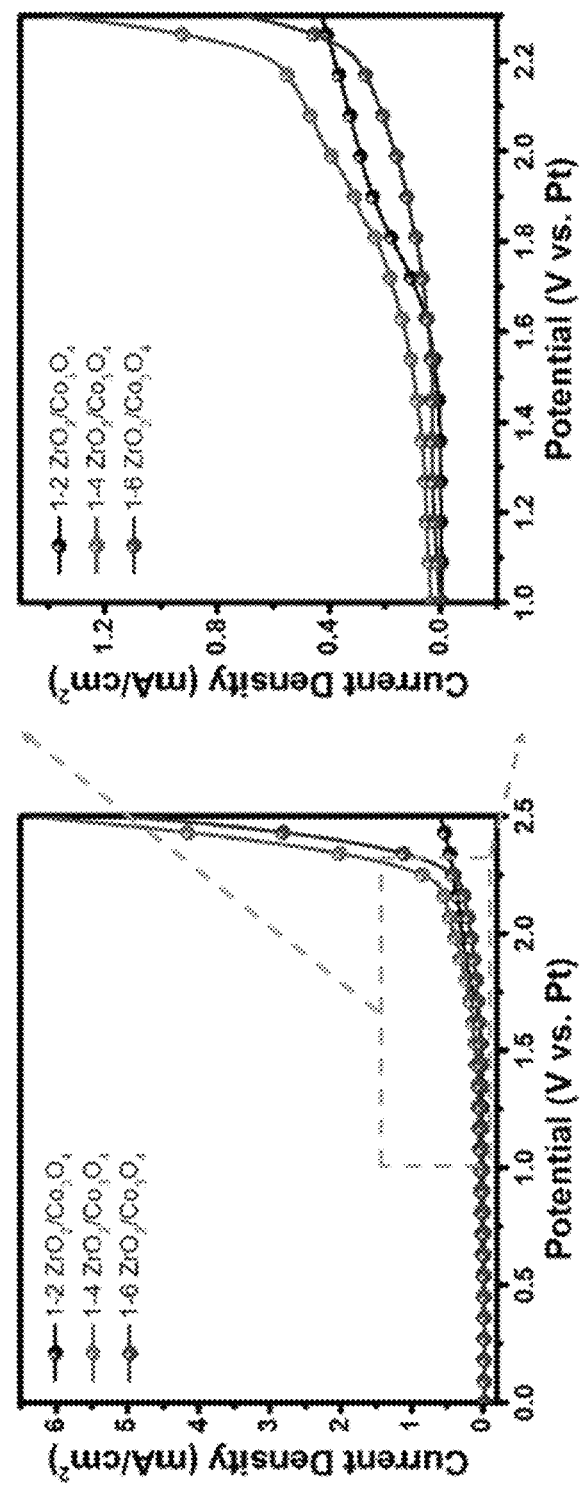
FIG. 6 shows the linear sweep voltammetry (LSV) curve of $ZrO_2/Co_3O_4$ in $CH_4$-saturated carbonate electrolyte.

FIG. 6 shows the linear sweep voltammetry (LSV) curve of $ZrO_2/Co_3O_4$ in a $CH_4$-saturated carbonate electrolyte. It can be seen from FIG. 6 that 1-4 $ZrO_2/Co_3O_4$ sample shows the highest electrochemical current density for $CH_4$ oxidation, and has a relatively suitable size and $Co_3O_4$ content. In addition, 1-2 $ZrO_2/Co_3O_4$ sample shows relatively low current density even after increasing the potential to a high level. This is because such a small amount of $Co_3O_4$ lowers the activity of catalyst in $CH_4$ oxidation. On the contrary, $ZrO_2$ shows significantly weak oxidation activity in a saturated state of water and methane due to a band gap larger than 5 eV. Further, 1-6 $ZrO_2/Co_3O_4$ sample and 1-4 $ZrO_2/Co_3O_4$ sample show the same J-V curve tendency but show relatively low current density. This is because the surface adsorption ability of carbonate ions is low due to a lower amount of $ZrO_2$.

Test Example 4: Determination of Methane Conversion and Analysis of Product

Figure 7:
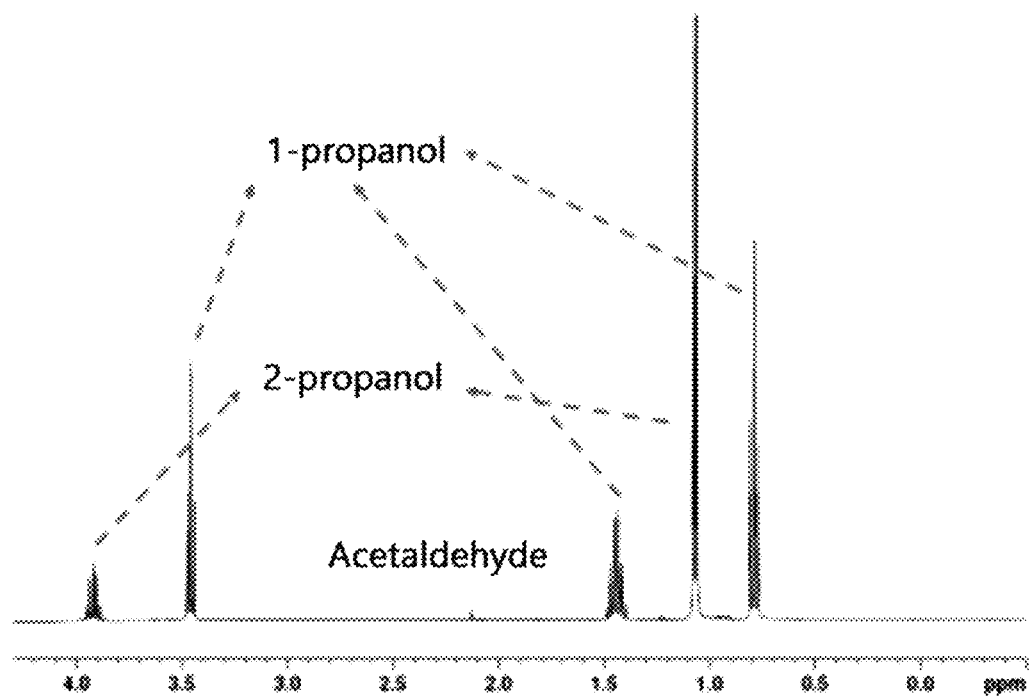
FIG. 7 shows $^1$H-NMR spectrum of the reaction product after carrying out reaction for 12 hours.

FIG. 7 shows $^1$H-NMR spectrum of the reaction product after carrying out reaction for 12 hours. Referring to FIG. 7, the main product includes 1-propanol and 2-propanol but methanol, ethanol, acetaldehyde and acetone are also observed as byproducts. A typical 1H-NMR peak of methanol is positioned at 3.3-3.5 ppm and may be overlapped with the peak of 1-propanol. A 1H-NMR peak of ethanol appears at the same position as the peak of 2-propanol. However, the number of sub-peaks of ethanol is different from that of 2-propanol. Therefore, it is thought that the product is 2-propanol. However, small ethanol peaks having weak peak intensity may be obscured by the peaks of 2-propanol. A small peak at 2.2 ppm may be generated by acetaldehyde and acetone. As compared to the main products, 1-propanol and 2-propanol, all byproducts are observed in a neglectable amount.

Figure 8:
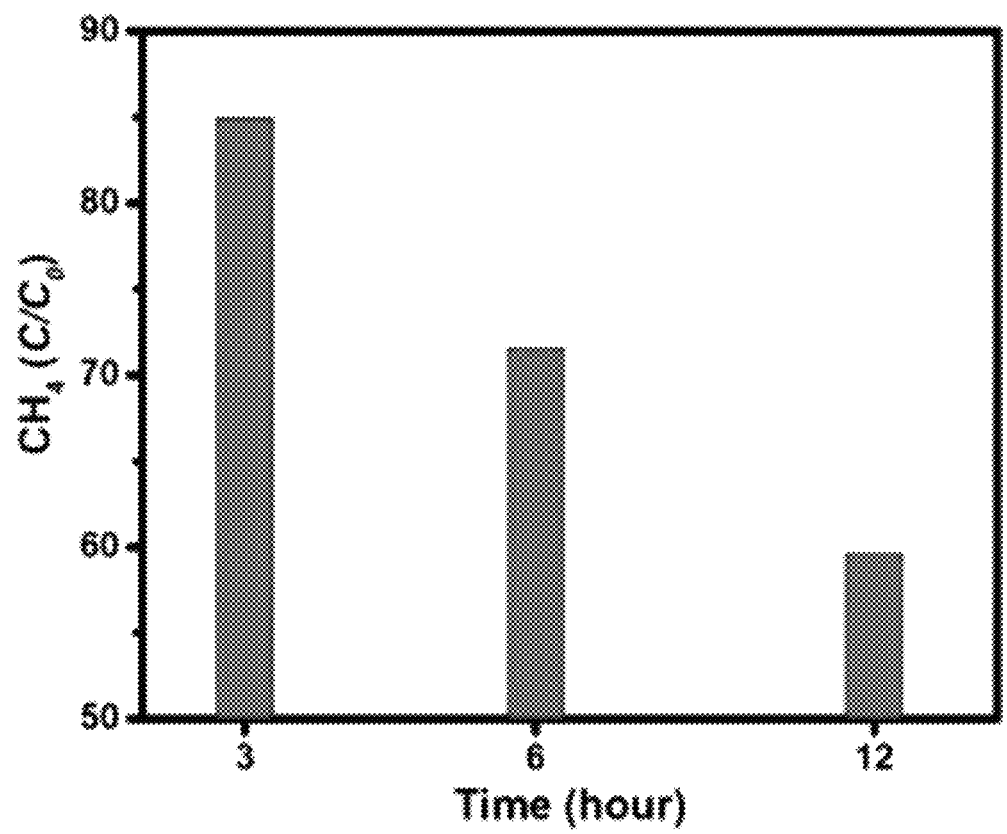
FIG. 8 shows the amount of $CH_4$ remaining in the reactor after carrying out reaction for 3, 6, or 12 hours.

FIG. 8 shows the amount of CH$_4$ remaining in the reactor after carrying out reaction for 3, 6, or 12 hours. Referring to FIG. 8, consumption of CH$_4$ and production of the products can be determined by carrying out gas chromatography (GC) and GC-mass spectrometry (MS) as a function of time.

CH$_4$ gas is substantially consumed and the consumption is decreased as a function of reaction time. After carrying out reaction for 12 hours, about 40% of methane gas is converted, while various products are determined through a GC-MS system. The results are shown in the following Table 1.

TABLE 1

| Reaction time [h] | Methanol [μg mL$^{-1}$] | Formaldehyde [μg mL$^{-1}$] | Ethanol [μg mL$^{-1}$] | Acetaldehyde [μg mL$^{-1}$] | 1-propanol [μg mL$^{-1}$] | 2-propanol [μg mL$^{-1}$] | Acetone [μg mL$^{-1}$] |
|---|---|---|---|---|---|---|---|
| 3 | 29.95 | 0.88 | 0 | 261.50 | 0.50 | 19.53 | 0 |
| 6 | 33.15 | 1.11 | 0.49 | 170.34 | 56.51 | 101.74 | 3.82 |
| 12 | 33.71 | 1.10 | 35.21 | 153.42 | 1336.12 | 1315.56 | 14.16 |

According to Table 1, the seven kinds of products, methanol, formaldehyde, ethanol, acetaldehyde, 1-propanol, 2-propanol and acetone are analyzed.

The amount of products containing one carbon atom, methanol and formaldehyde, is not changed significantly with time, which suggests a balance between production and consumption. Therefore, methanol and formaldehyde are the first products of methane oxidation. It is known that formaldehyde is an oxidation product of methanol. After comparing the amount of products containing two carbon atoms, ethanol and acetaldehyde, with each other, it is determined that acetaldehyde is a main product of the addition reaction between methane and formaldehyde. Further, the amount of acetaldehyde is decreased with time, which suggests that acetaldehyde plays a key role in production of 1-propanol and 2-propanol. After carrying out reaction for 12 hours, 1-propanol and 2-propanol become main stable products of methane oxidation, which corresponds to the results of 1H-NMR.

Figure 9:
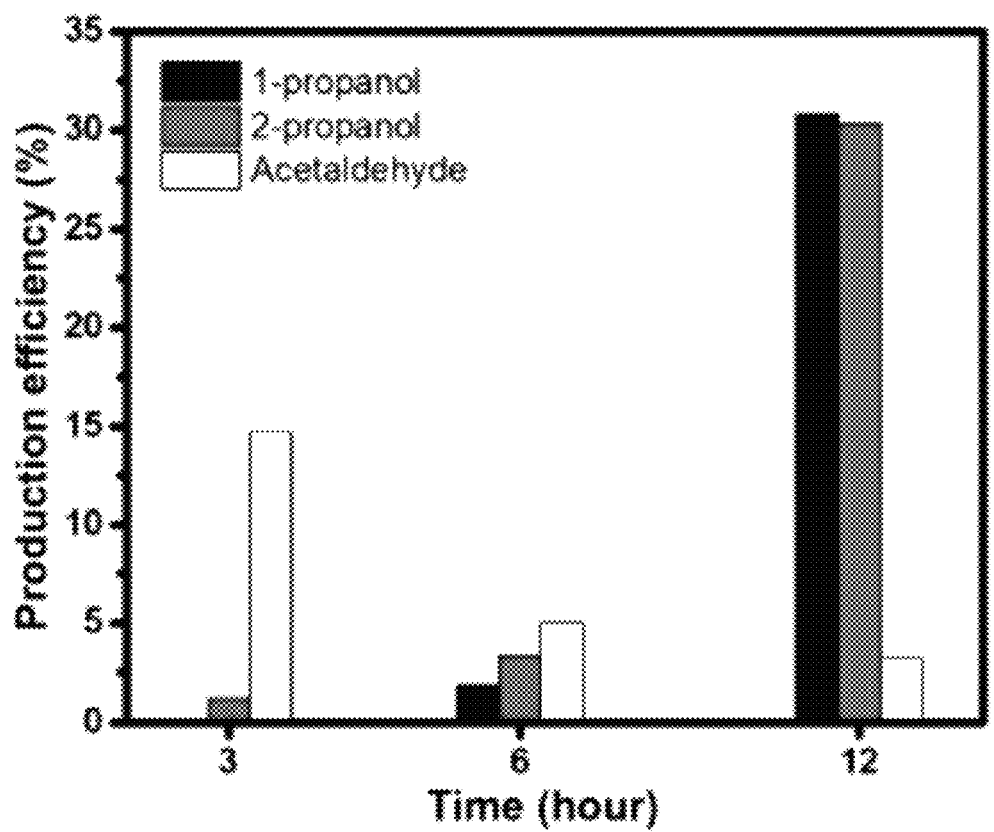
FIG. 9 shows the results of calculation of conversion efficiency into acetaldehyde, 1-propanol and 2-propanol.

FIG. 9 shows the results of calculation of conversion efficiency into acetaldehyde, 1-propanol and 2-propanol. After carrying out reaction for 12 hours, it is shown that the main products, 1-propanol and 2-propanol, show a total production efficiency of 60% or more.

Acetaldehyde is an important product. Production of acetaldehyde is depicted in the following Reaction Scheme.

[Reaction Scheme]

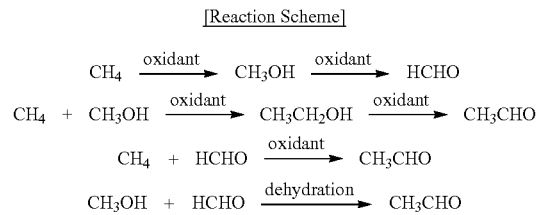

In the main reaction related with methane oxidation, methane is oxidized by an oxidant (carbonate) to form methanol, which is oxidized continuously to form formaldehyde. Then, several reactions occur to form methane, methanol and formaldehyde from methane, methanol and formaldehyde as reactants. Therefore, production and accumulation of acetaldehyde occur promptly and significantly, which corresponds to the results of Table 1.

Figure 10:
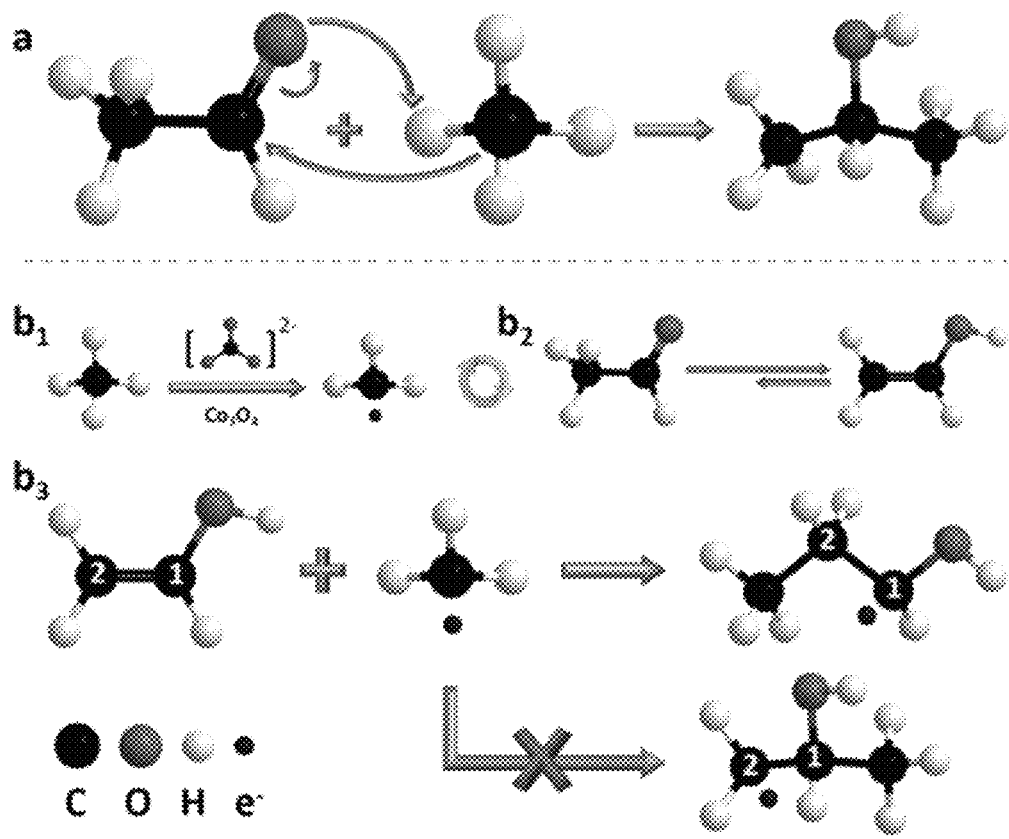
FIG. 10 shows a mechanism of production of 1-propanol and 2-propanol from acetaldehyde.

FIG. 10 shows a mechanism of production of 1-propanol and 2-propanol from acetaldehyde. The process is the most important reaction of methane conversion. According to the reaction of (a), the methyl group of methane functions as a nucleophilic agent and attacks the carbonyl carbon of acetaldehyde. Therefore, nucleophilic addition occurs to form one of the main products in conversion of methane, i.e. 2-propanol. However, considering the addition mechanism, it is not possible to produce 1-propanol from acetaldehyde and methane. To search a route capable of producing 1-propanol, all reaction conditions are considered. As shown in (b1)-(b3), it can be seen that free radical addition is suitable.

First, in route (b1), Co$_3$O$_4$ and carbonate participate in formation of methyl radicals from methane. Since carbonate radicals have a relatively low production energy as compared to hydroxyl radicals, they may be produced through anodic oxidation with the aid of Co$_3$O$_4$ during electrochemical oxidation. The carbonate radicals function as intermediates to produce methyl radicals from the reaction of methane.

In route (b2), acetaldehyde maintains an equilibrium between isomers, acetaldehyde and vinyl alcohol. Although the arrangement of vinyl alcohol requires an energy higher than formation of acetaldehyde by 45 kJ mol$^{-1}$, the energy may be accomplished in the presence of carbonate. In general electrophilic addition into alkenes, the product follows the Markovnikov's rule, which suggests that reaction of methane with vinyl alcohol produces 2-propanol as a main product.

However, when addition is carried out through a free radical route as shown in route (b3), the main product becomes 1-propanol since the product follows the anti-Markovnikov's rule. When a methyl radical attacks carbon 1, a 2-propanol radical (free electron of carbon 2) is not in the most stable state. However, when a methyl radical attacks carbon 2, a 1-propanol radical (free electron of carbon 1) is more stable than the 2-propanol radical, which suggests that 1-propanol is the main product. It is possible to convert acetaldehyde and methane directly into 2-propanol through nucleophilic addition. In addition, 2-propanol is produced in a larger amount as compared to 1-propanol within a short oxidation time. However, after long-term reaction, the amount of 1-propanol is larger than that of 2-propanol, even though 2-propanol is more thermodynamically stable. This explains specific local selectivity of 1-propanol production through radical addition in which the Co$_3$O$_4$ catalyst and carbonate electrolyte participate.

In addition, although the present disclosure does not provide particular test results, it is shown that the ZrO$_2$/Co$_3$O$_4$ nanocomposite catalyst coated with graphene according to Example 1-3 shows significantly improved catalytic activity in methane oxidation as compared to the ZrO$_2$/Co$_3$O$_4$ nanocomposite catalyst.

Further, the $ZrO_2/NiCo_2O_4$ nanocomposite catalyst obtained by using a Ni—Co alloy or composite, $NiCo_2O_4$, as a catalyst support according to Example 1-2 shows improved catalytic activity as compared to the $ZrO_2/Co_3O_4$ nanocomposite catalyst using $Co_3O_4$ support according to Example 1-1, as can be seen from an upward shift of the J-V curve for methane oxidation. In addition, it can be seen from a left shift of the onset point that the $ZrO_2/NiCo_2O_4$ nanocomposite catalyst shows improved catalytic activity capable of initiating methane oxidation. Additionally, the $ZrO_2/NiCo_2O_4$ nanocomposite catalyst coated with graphene according to Example 1-4 specifically shows improved anti-poisoning property and durability as compared to the other groups of catalysts according to the present disclosure.

While the present disclosure has been described with respect to the specific embodiments, it will be apparent to those skilled in the art that various changes and modifications may be made through addition, modification, elimination or addition of constitutional elements without departing from the spirit and scope of the disclosure as defined in the following claims.

What is claimed is:

1. An electrochemical catalyst for conversion of methane gas, which comprises:
    a conductive substrate selected from graphite paper, graphene, carbon black, copper, nickel and alumina;
    a catalyst composite layer for conversion of methane gas, formed on the conductive substrate; and
    optionally, a cover layer for protecting the catalyst composite layer for conversion of methane gas,
    wherein the catalyst composite layer comprises a support and $ZrO_2$ nanoparticles adsorbed to the surface of the support, wherein the support has a structure of $Co_3O_4$ nanoplates or $NiCo_2O_4$ nanowires, and the catalyst composite is used for converting methane gas into alcohols.

2. The electrochemical catalyst for conversion of methane gas according to claim 1, wherein when the support is $Co_3O_4$ nanoplates, the elemental ratio of Co to Zr in the catalyst composite may be 0.2:1-6.5:1, and
    when the support is $NiCo_2O_4$ nanowires, the elemental ratio of Zr:Ni:Co in the composite may be 0.1-2.5:2-3:5.

3. The electrochemical catalyst for conversion of methane gas according to claim 1, which is coated with graphene.

4. The electrochemical catalyst for conversion of methane gas according to claim 3, wherein the $ZrO_2$ nanoparticles have an average particle diameter of 10 nm-1 μm, and the $Co_3O_4$ nanoplates have an average particle diameter of 1 μm -10 μm.

5. The electrochemical catalyst for conversion of methane gas according to claim 1, wherein the $ZrO_2$ nanoparticles have a spherical shape, rod-like shape, hollow shape, or an ellipsoidal solid shape.

6. The electrochemical catalyst for conversion of methane gas according to claim 1, wherein the adsorption is physical adsorption.

7. A method for preparing an electrochemical catalyst for conversion of methane gas as claimed in claim 1, comprising the steps of:
    (a) introducing $ZrOCl_2$ hydrate, $Co(NO_3)_2$ hydrate and hydroxide to water and dissolving them therein to obtain an aqueous precursor solution;
    (b) heating the aqueous precursor solution to 150-250° C. to precipitate $ZrO_2/Co_3O_4$ composite powder;
    (c) carrying out centrifugal separation of the product of step (b) to obtain $ZrO_2/Co_3O_4$ powder; and
    (d) washing and drying the $ZrO_2/Co_3O_4$ powder of step (c) and carrying out heat treatment at 400-600° C. to obtain a $ZrO_2/Co_3O_4$ catalyst composite.

8. The method for preparing a catalyst composite for conversion of methane gas according to claim 7, wherein the hydroxide is any one selected from Na(OH), K(OH), $Ca(OH)_2$ and $Sr(OH)_2$.

9. The method for preparing a catalyst composite for conversion of methane gas according to claim 7, wherein the $ZrOCl_2$ hydrate and $Co(NO_3)_2$ hydrate are mixed at a molar compositional ratio of 1:1-1:6.

10. A method for conversion of methane gas, comprising: carrying out electrochemical oxidation of methane gas at a graphite electrode surface-coated with the $ZrO_2/Co_3O_4$ electrochemical catalyst as defined in claim 1 to convert methane gas into alcohols.

11. The method for conversion of methane gas according to claim 10, wherein the coating is carried out by adding a dispersion of the $ZrO_2/Co_3O_4$ catalyst composite in water to a graphite electrode, followed by drying.

12. The method for conversion of methane gas according to claim 10, wherein the electrode surface-coated with the $ZrO_2/Co_3O_4$ catalyst composite is further coated with a protective layer on the catalyst composite layer.

13. The method for conversion of methane gas according to claim 10, which further comprises a step of removing oxygen through bubbling of methane in a carbonate electrolyte before the electrochemical oxidation.

14. The method for conversion of methane gas according to claim 10, wherein the final product obtained by the electrochemical oxidation comprises at least one selected from 1-propanol, 2-propanol, methanol, formaldehyde, ethanol, acetaldehyde and acetone.

15. The method for conversion of methane gas according to claim 14, wherein 1-propanol and 2-propanol are produced from acetaldehyde.

16. The method for conversion of methane gas according to claim 15, wherein 1-propanol and 2-propanol are produced through nucleophilic addition and free radical addition.

17. The method for conversion of methane gas according to claim 10, wherein the electrochemical oxidation is carried out at room temperature under ambient pressure, or under pressure to increase the solubility of methane.

* * * * *